United States Patent [19]

Amor et al.

[11] Patent Number: 5,279,592
[45] Date of Patent: Jan. 18, 1994

[54] CATHETER FOR MEDICAL USE

[75] Inventors: Max Amor, Vandoeuve Les Nancy; Gilles Karcher; Gerard Ethevenot, both of Nancy, all of France

[73] Assignee: Medicorp Research Laboratory Corporation, Boca Raton, Fla.

[21] Appl. No.: 411,020

[22] Filed: Sep. 22, 1989

[30] Foreign Application Priority Data

Sep. 22, 1988 [FR] France .................. 88 12564

[51] Int. Cl.⁵ ............................................. A61M 5/00
[52] U.S. Cl. .................................. 604/264; 604/283; 604/905
[58] Field of Search ............... 604/264, 280, 281, 282, 604/283, 905

[56] References Cited

U.S. PATENT DOCUMENTS

| | | |
|---|---|---|
| 4,254,773 | 3/1981 | Waldbillig ........................ 604/283 |
| 4,526,572 | 7/1985 | Donnan et al. ................... 604/283 X |
| 4,621,634 | 11/1986 | Nowacki et al. ................. 604/905 X |
| 4,676,241 | 6/1987 | Webb et al. ...................... 604/280 X |

Primary Examiner—John D. Yasko
Attorney, Agent, or Firm—Sandler Greenblum & Bernstein

[57] ABSTRACT

Catheter for medical use is provided with a main tube having a distal end and a proximal end, and a mechanism for connection to an external apparatus. To assist in the manipulation of the catheter maneuvering means are provided at the proximal end which allow rotary control of at least the main tube in contact with the connection mechanism.

17 Claims, 1 Drawing Sheet

CATHETER FOR MEDICAL USE

BACKGROUND OF THE INVENTION

1. Field of the Invention

The invention relates to a catheter for medical use which is devised to be introduced into the body of an person for endoscopy, for the injection of a diagnostic liquid, or for a therapeutic purpose. The catheter includes a main tube having a distal end and a proximal end, and is provided with means for connection to external apparatus.

The invention has application in the medical field, and more particularly concerns the specialized manufacturing industry in the design of implements intended, specifically, for use in this area.

2. Discussion of Background and Relevant Material

Catheters are apparatus used more and more for performing, by percutaneous means, either particular treatments of certain organs, or simply for exploring the latter.

One of the illnesses helped by catheters is, for example, arthritis. This illness consists of, in fact, a narrowing of the blood vessels of atheromatis origin resulting in either a partial obstruction, by a stenosis, or a complete obstruction, with thrombosis resulting from this state.

In a number of cases of arthritis, the arterial deobstruction is carried out by percutaneous means by way of a balloon catheter to force the stenosis to open.

Elsewhere, angiography, which is a radiography of the blood vessels, frequently needs the use of catheters to inject into the veins or arteries of a given region, an opaque substance to view the vessels by means of X-rays.

In all instances of its use, the catheter consists of a main tube provided with a distal and having a shape according to the cavities to be reached. This main tube also comprises a proximal end provided with means for permitting connection of the catheter to external apparatus, such as a valve or an intermediate or other coupling means.

More precisely, these means for connection comprise a cylindrical body have a central bore matching the external diameter of the main tube of the catheter to thereby allow engagement with the proximal end of the latter.

The cylindrical body is made integral with the main tube, by moulding by adhering, or by a solvent method. It is also lengthened at its free end by a cylindrical coupling of universal type.

Thus, the coupling connection is of cylindrical shape and comprises a coaxial pipe having a slight conicity at its inner end, reducing along its section. This pipe is situated in the bore of the main tube of the catheter, and is made to receive, quite precisely, the collar of the matching joint associated with the external apparatus. The coupling additionally comprises at its free end and on its external periphery, notches used to cooperate with a thread present with the matching joint means.

As seen from the above description of a catheter according to the prior state of the art, it is seen that once joined to an apparatus or external tube, the mobility of this catheter is strictly dependent on the mobility of the external apparatus.

Now, it is quite clear that in the course of its progress in the body of the patient, it must be possible to easily orient the distal end of the catheter in such a way as to reach the organ with which it is required to investigate or treat. This orientation only capable of being achieved while imparting an axial displacement or a rotation of the external part of the catheter. To that end, it should be noted that the main tube is generally made rigid, either because of the presence of a wire mandrel introduced into the interior opening, or by means of a braided structure embedded into the thickness of the main tube.

However, in the case where the external apparatus or the tube connected to the catheter are relatively cumbersome, there is inevitably, a limited maneuverability and, in all cases, not very convenient. Besides, depending on the rotation given to the catheter, a smaller resistance even with the apparatus or the tube accompanying its movement could effect a disconnection in any area of the system and, lastly, alter the operation or measurement in progress.

With this object, it is known to conceive the joints, such as taught in the document US-A-4254773, to allow the rotation of the tubes or the elements which are joined one to another. Also, in inserting such a rotary joint between means for connecting the catheter and the tube or the external apparatus, the operator is instigating the rotation of the catheter without imparting to this apparatus or this external tube any identical movement.

However, there are disadvantages associated with these joint means, which include a supplementary element of which it is necessary to keep a supply and store at the medical establishment. Besides, it contributes to additional expenses.

Additionally, this rotary joint introduces the disadvantage that it does not provide any solution to the possible disconnections as described above, but whichever part is manipulated by the operator, i.e. the rotary joint or the catheter, the movement is transmitted less through the connection, thus separating the catheter and the rotary joint. In addition, it should be noted that the proximity of the latter and the means for coupling the catheter may lead the operator to making an incorrect movement, and inevitably, provoke a disconnection.

SUMMARY OF THE INVENTION

The present invention has as its object to remedy the above-discussed disadvantages by providing a catheter which is provided with appropriate means allowing it to have a rotation without having this last effect on an apparatus or external tube through any one of the system connections.

The invention solves this problem by producing a catheter for medical use, for introduction into the body of a person, for the injection of a diagnostic liquid, or for a therapeutic purpose, having a main tube provided with a distal end and a proximal end, this being provided with means for connection to an external apparatus. Moreover, the cathiter includes at its proximal end, maneuvering means allowing the control, by rotation, of at least the main tube with regard to the connection means.

By the above, it clearly has the advantage that the risks of sudden disconnection are removed and that the provision and use of a subsidiary element is not needed.

BRIEF DESCRIPTION OF THE DRAWINGS

The invention is described hereinafter in more detail with the aid of the drawings which represent merely one embodiment.

DESCRIPTION OF THE PREFERRED EMBODIMENTS

Figure 1:
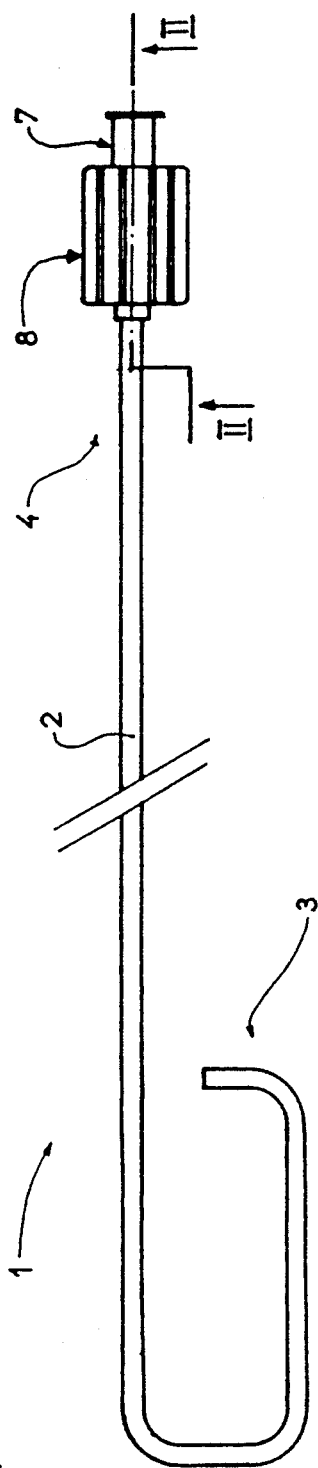
FIG. 1 illustrates a schematic plan view of a catheter according to the invention.
Figure 2:
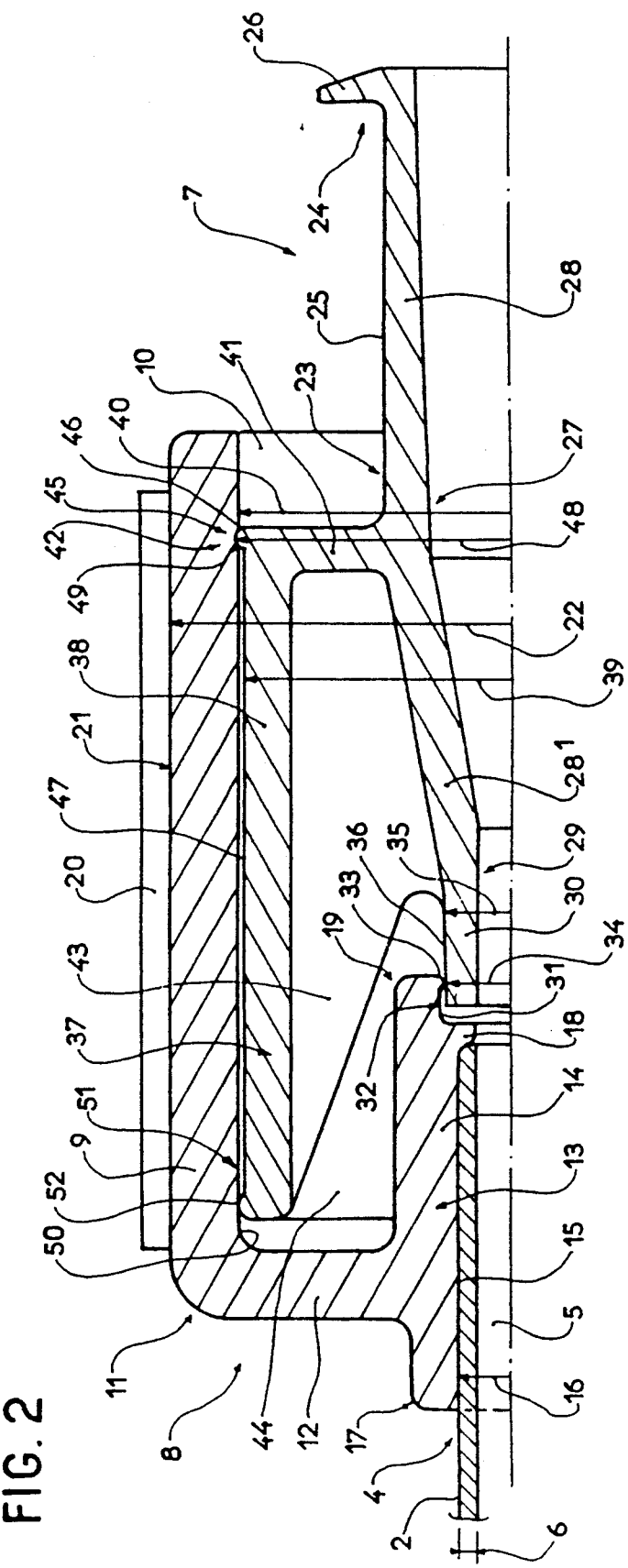
FIG. 2 illustrates a view along line II—II in FIG. 1.

The present invention relates to a catheter whose particular embodiment is illustrated in FIG. 1.

The catheter is for medical use and intended particularly to be introduced into a person's body for examination, for use in endoscopy, for injecting diagnostic liquid, or for therapeutic use in connection with a specific organ. Of course, it will be understood that the catheter, which is the object of the present invention, is not at all limited to the medical uses described above, and there exists, today, many other therapeutic or diagnostic techniques in which catheters arise.

However, according to the use for which it is ascribed, a catheter 1 comprises a main tube 2 of variable length and diameter and having a distal end 3 of shape predetermined depending on the organ which it is intended to reach in order to examine or provide a treatment.

The main tube 2 is, generally, of a flexible or semi-rigid nature, so as to readily adapt to the sizes of the passages in which it is to be used. Also, the materials usually used in its manufacture are thermoplastics of medical quality. Those most often encountered are polyurethane and polyethylene because of their inert nature with regard to the media carried and the physiological substances into which the catheter is brought into contact. It may even be made of a metal resistant to corrosion by blood, saline solutions, and all other substances of a physiological or therapeutic nature.

In the case of its being made of thermoplastic, the main body of the tube is made rigid so as to facilitate its orientation from the proximal end 4, external to the patient. Two techniques are in use today:

either a wire mandrel is used, introduced into the internal housing 5 of the catheter 1 at the time it is put into the patient's body, then withdrawn following examination or treatment;

or, embedded into the thickness 6 of the main tube 2, using known techniques, is a braided structure, in this case, however, to ensure that the distal end 3 maintains its flexibility so the organs met are not injured.

In addition, the catheter 1 and, in particular the main tube 2, comprises at its proximal end 4, universal connection means 7, allowing its coupling to an external apparatus, such as a transfer pipe, a valve or other means.

At the proximal end 4 of the main tube 2 are likewise arranged, according to the invention, maneuvering means 8 allowing control of at least rotation of the main tube 2 by connection to the connection means 7.

Until now, this possibility of simple manipulation was only possible by separate means, and more precisely, by rotary couplings. Nevertheless, these result in the inconvenience of being unsafe because of the risks of disconnection which result. Moreover, they require a supplementary element, of which it is inconvenient to keep a supply and to store in places of use.

By combining, directly, the means of for maneuvering with the catheter 1, the present invention remedies these inconveniences.

Preferably, the means for maneuvering 8 are directly bound to, on the one hand the main tube 2, and, on the other hand, the connection means 7.

Thus, according to a preferred embodiment, these means for maneuvering 8 comprise a body 9 of tubular shape, having a central bore 10 and provided with, at one of the end 11, an annular web 12. This carries, at its center a sleeve 13, part of which 14 extends into the central bore 10 of the body 9. This sleeve 13 has a bore 15 situated in the axial extension of the central bore 10 and machined to the external diameter 16 of the main tube 2.

Thus, when the catheter 1 is assembled, the proximal end 4 of the main tube 2 may be introduced, into the external end 17 of the sleeve 13 in the bore 15 until it stops against the internal peripheral lip 18 arranged on the internal wall of the latter and, more precisely, in proximity to the end 19 of the portion 14 shown in the central bore 10. Then, the sleeve 13 is made integral with the main tube 2, either by glueing, or by moulding or by use of a solvent, in the case where the materials used allow it. With regard to this, it is convenient to note that the maneuvering mean 8 may be made from an identical material to that of the main tube 2, and, preferable, from a thermoplastic such as polyethylene or polyethylane.

Thus, after assembly, the movement given to the body 9 by the maneuvering means 8 is directly transmitted to the main tube 2 of the catheter 1. It is noted that, to facilitate gripping of the body 9, it may have a polygonal cross-section or comprise a series of ridges 20 distributed around the external surface of cylindrical shape 21 and disposed along its generatrices. Moreover, the diameter 22 of the body 9 will be arranged so that the control means of two fingers will generate sufficient torque on the catheter to guarantee its rotation.

As for the connection means 7, they comprise an extension 23, formed from a cylindrically-shaped member 28 and a truncated cone shaped member 281. In particular, the cylindrically shaped member 28 carries at its free end 24, and on its external surface 25, lugs 26 arranged to cooperate with the thread of the coupling means of an apparatus or an external pipe (not shown). As for the truncated cone shaped member 281, a continuation of the cylindrically-shaped member 28, it has, at its tapered end 29, a cylindrically-shaped portion 30. This, more precisely, is intended to be introduced, partially and as far as the internal end 19, into the sleeve 13 of the maneuvering means 8. Also, the bore 15 of the sleeve 13 comprises, beyond the internal peripheral lip 18 acting as a stop for the main tube 2, an unlatching member 31 of diameter slightly greater than the external diameter 35 of the cylindrical portion 30. This bore 15 is further provided at the end 32, pointing towards the central bore 10, an internal ridge 33, the diameter 34 reducing in a manner to match, or preferably, to be slightly smaller than the external diameter 35 of the cylindrical portion 30. This arrangement permits the introduction, with a little force, of the cylindrical portion 30 into the coupling 13 by pushing away the internal ridge 13 by the elastic effect of the thermoplastic material. Eventually, the internal ridge 33 cooperates with a positive pressure with the external surface 36 of the cylindrical portion 30 and guarantees the tightness between the maneuvering means 8 and the connection means 7.

There is also provided means for rotation 37 in the maneuvering means 8 consisting of a socket 38 which fits in the central bore 10 and thus has an external diameter 39 slightly less than the internal diameter of the latter. This socket 38 is integral with the extension piece 23, on the on hand, by means of a web 41 situated at its end 42 oriented in the direction of the cylindrical-shaped member 28 and, on the other hand, by means of intermediate strengthening ribs 43. These latter are variable in number arranged around the internal part of the socket 38 and cooperate, quite precisely, with the truncated cone shaped member 281 of the extension 23.

This socket 38 further comprises means 45 for keeping the connection means 7 joined to the maneuvering means 8. Preferably, such means 45 consist of a peripheral ridge 46 edging the external surface 47 of the socket 38 at its end 42. This ridge 46 has a diameter 48 slightly larger than the diameter 40 of the central bore 10 or the body 9 so that, after engagement, with a slight force, of the connection means 7 into the maneuvering means 8, the peripheral ridge 46 becomes engaged in a groove 49 machined in the internal surface 50 of the body 9. Thus the peripheral ridge 46 provides a means for preventing translatory movement of the connection means 7 with respect to the maneuvering means 8, and by the same means, provided a perfect guiding means for rotation of the socket 38 in the central bore 10 of the body 9.

Advantageously, there is found at the free end 51 of the socket 38, and on its external surface 47, a ridge 52 cooperating with a reduced clearance, with the internal surface 50 of the body 9 in manner to assist in the rotational guiding, in ideal conditions, of the connection means 7 by contact with the maneuvering means 8.

As can be seen from the preceding description, the present invention whilst being complex, has substantial advantages for catheters for medical use. On the one hand, it allows complete maneuverability without, on the other hand, the risks of disconnection known until now.

We claim:

1. Catheter for medical use comprising:
   a main tube having a distal end and a proximal end;
   means for connecting said proximal end of said main tube to an external apparatus; and
   maneuverable means fixedly connected to said main tube and connected in a rotary manner to said means for connecting for permitting rotary control of at least said main tube, said maneuverable means including a body having a central bore forming an interior portion with a sleeve extending in said central bore, and said sleeve including a bore having an inside diameter that corresponds to an outside diameter of said main tube, and said proximal end of said main tube being inserted into said bore.

2. The catheter according to claim 1, wherein said centrally located sleeve is attached to one end of said body by an annular web.

3. The catheter according to claim 2, wherein said sleeve is centrally positioned on said annular web.

4. The catheter according to claim 3, wherein said maneuverable means is fixedly connected to said main tube by molding, adhesion or solvent connection.

5. The catheter according to claim 1, wherein said body having an external surface having ridges to permit the transmission of force exerted by an operator to the catheter.

6. The catheter according to claim 5, wherein said body has a polygonal cross-section.

7. The catheter according to claim 5, wherein said body has a cylindrical cross-section.

8. Catheter for medical use comprising:
   a main tube having a distal end and a proximal end;
   means for connecting said proximal end of said main tube to an external apparatus; and
   maneuverable means fixedly connected to said main tube and connected in a rotary manner to said means for connecting for permitting rotary control of at least said main tube, said maneuverable means including a body having a central bore forming an interior portion and an annular web at one end, said annular web including a centrally located sleeve having a portion that extends into said interior portion, said sleeve including a bore having an inside diameter that corresponds to an outside diameter of said main tube, said proximal end of said main tube being inserted into said bore, and said sleeve including on its internal surface an internal peripheral lip against which said proximal end of said main tube abuts when introduced into said bore.

9. Catheter for medical use comprising:
   a main tube having a distal end and a proximal end;
   means for connecting said proximal end of said main tube to an external apparatus, said means for connecting including an extension member composed of a truncated cone-shaped member having two ends, with a cylindrical extension member axially extending from one end and a cylindrical portion extending from the other end, said cylindrical extension member including a free end having an external surface having lug means for coupling to an external apparatus; and
   maneuverable means fixedly connected to said main tube and connected in a rotary manner to said means for connecting for permitting rotary control of at least said main tube, said maneuverable means including a body having a central bore forming an interior portion, an annular web at one end, said annular web including a centrally located sleeve having a portion that extends into said interior portion and arranged to cooperate with said cylindrical portion.

10. The catheter according to claim 9, wherein said centrally located sleeve includes an axially extending bore and an external surface, and a lip positioned on said external surface.

11. The catheter according to claim 10, wherein said lip is positioned on one end of said centrally located sleeve, and said one end of said centrally located sleeve includes means for unlatching of slightly larger inside diameter than the outside diameter of said cylindrical portion.

12. The catheter according to claim 11, wherein said centrally located sleeve includes, at said one end, an internally directed ridge which is arranged to contact an external surface of said cylindrical portion under a positive force to thereby provide said cooperation between said centrally located sleeve and said cylindrical portion.

13. The catheter according to claim 9, further including means for enabling rotation including a socket having an outside diameter slightly smaller than the inside diameter of said central bore.

14. The catheter according to claim 13, wherein said socket is integrally attached to said extension member by an annular web attached to one end of said socket, and by intermediate strengthening ribs arranged to cooperate with said truncated cone-shaped member.

15. The catheter according to claim 14, wherein said socket includes means for maintaining connection between said means for connection and said maneuverable means.

16. The catheter according to claim 15, wherein said means for maintaining connection include a peripheral ridge externally mounted on said one end of said socket, with said peripheral ridge being arranged to engage a groove in an interior surface of said central bore.

17. The catheter according to claim 16, wherein said socket includes a free end opposite to said one end of said socket, and said means for maintaining connection further include a ridge provided on said free end for cooperating with a positive force against said interior surface of said central bore.

* * * * *